United States Patent

Brockwell et al.

[11] Patent Number: 6,057,481
[45] Date of Patent: May 2, 2000

[54] PROCESSES FOR THE MANUFACTURE OF METHYLMERCAPTOPROPANAL

[75] Inventors: Jonathan L Brockwell; Mark A Young, both of South Charleston; William G Etzkorn, Hurricane; Barbara K Warren; John M Maher, both of Charleston, all of W. Va.

[73] Assignee: Union Carbide Chemicals & Plastics Technology Corporation, Danbury, Conn.

[21] Appl. No.: 09/155,750

[22] PCT Filed: Mar. 27, 1997

[86] PCT No.: PCT/US97/05100

§ 371 Date: Oct. 1, 1998

§ 102(e) Date: Oct. 1, 1998

[87] PCT Pub. No.: WO97/36848

PCT Pub. Date: Oct. 9, 1997

Related U.S. Application Data

[60] Provisional application No. 60/014,507, Apr. 1, 1996, provisional application No. 60/014,678, Apr. 1, 1996, and provisional application No. 60/014,510, Apr. 1, 1996.

[51] Int. Cl.[7] .............................................. C07C 319/02
[52] U.S. Cl. ................................................................ 568/41
[58] Field of Search .................................. 568/41, 469.9, 568/470

[56] References Cited

U.S. PATENT DOCUMENTS

| | | |
|---|---|---|
| 2,626,282 | 1/1953 | Cunningham . |
| 2,676,190 | 4/1954 | Bernard . |
| 3,438,868 | 4/1969 | Yoshitsugu . |
| 3,529,940 | 9/1970 | Shima . |
| 4,048,232 | 9/1977 | Koberstein . |
| 4,225,516 | 9/1980 | Biola . |
| 4,319,047 | 3/1982 | Komorn . |
| 4,999,452 | 3/1991 | Bunning et al. ........................ 560/208 |
| 5,155,262 | 10/1992 | Etzkorn et al. ........................ 562/532 |
| 5,183,936 | 2/1993 | Etzkorn et al. ........................ 562/532 |
| 5,198,578 | 3/1993 | Etzkorn et al. ........................ 562/532 |
| 5,243,082 | 9/1993 | Etzkorn et al. ........................ 568/465 |
| 5,321,180 | 6/1994 | Davis ...................................... 585/431 |
| 5,352,837 | 10/1994 | Hsu et al. ................................. 568/41 |
| 5,354,915 | 10/1994 | Reichle ................................. 568/881 |
| 5,637,766 | 6/1997 | Hsu . |
| 5,663,409 | 9/1997 | Blackburn . |
| 5,696,282 | 12/1997 | Shaw et al. ............................. 560/152 |
| 5,705,684 | 1/1998 | Hefner ................................... 562/547 |
| 5,744,647 | 4/1998 | Hsu . |

FOREIGN PATENT DOCUMENTS

| | | |
|---|---|---|
| 0117146 | 8/1984 | European Pat. Off. . |
| 0257565 | 3/1988 | European Pat. Off. . |

OTHER PUBLICATIONS

J.A. Chem Soc. 1948 vol. 70 pp. 1450–1451.

*Primary Examiner*—Shailendra Kumar
*Assistant Examiner*—Jean F Vollano
*Attorney, Agent, or Firm*—W. K. Volles

[57] ABSTRACT

Processes are disclosed for the conversion of propylene to methylmercaptopropanal by converting propylene to acrolein and converting acrolein to methylmercaptopropanal. The processes utilize oxygen and recycle propane to the acrolein reactor. Process feeds can comprise, propane, propylene or mixtures thereof. The presence of propane in the propylene-to-acrolein reaction can enhance the efficiency of the processes.

7 Claims, 3 Drawing Sheets

6,057,481

PROCESSES FOR THE MANUFACTURE OF METHYLMERCAPTOPROPANAL

This application is the national phase of PCT/U.S. 97/05100, filed Mar. 27, 1997; this application claims benefit of U.S. provisional applications No. 60/014507, filed Apr. 1, 1996, 60/014678, filed Apr. 1, 1996 and 60/014510, filed Apr. 1, 1996.

FIELD OF THE INVENTION

This invention relates to the manufacture of methylmercaptopropanal ("MMP"), also known in the art as 3-(Methylthio)-propanal, and more specifically relates to new processes for the conversion of propylene to MMP via an acrolein intermediate.

BACKGROUND OF THE INVENTION

MMP is an intermediate for the manufacture of both d, 1-methionine and 2-hydroxy-4-(methylthio)butanoic acid ("HMBA"). Methionine is an essential amino acid in which components of the animal feed compositions are commonly deficient. HMBA provides a source of methionine, and is widely used as a methionine supplement in animal feed formulations. MMP relatively free of impurities is typically required for the manufacture of HMBA or methionine.

MMP is conventionally produced by the reaction of acrolein with methyl mercaptan. In a conventional process for the preparation of MMP, acrolein and methyl mercaptan are introduced in a liquid phase into a reactor containing liquid-phase MMP product. The reaction takes place batchwise in the liquid phase. In order to produce MMP of the quality typically desired, refined acrolein is typically used in the manufacture of HMBA and methionine.

Acrolein is a highly toxic and flammable material. It is conventionally produced by the vapor-phase oxidation of propylene over a solid-phase catalyst, producing a crude, gaseous reaction product which contains acrolein, water vapor, acrylic acid, acetaldehyde, and other organic by-products. Typically, the gas is treated to remove acrylic acid, then contacted with cooled water for absorption of the acrolein. The resultant aqueous solution is distilled to recover the absorbed acrolein and other organic components. The crude acrolein is then refined to reject lower-boiling impurities such as, for example, acetaldehyde, producing a purified, liquid acrolein product. Since the conventional processes typically use a batch reaction system, condensation and in-process storage of liquid acrolein is necessary as a surge buffer between the acrolein process and the MMP reactor.

Storage of liquid acrolein involves significant toxicity, fire and explosion hazards. High capital and operating costs are consequently incurred in providing for the safe handling of acrolein. Substantial enhancements in the safety of handling acrolein would be achieved if acrolein were transferred directly and continuously from the acrolein manufacturing process to the MMP reactor without intermediate storage. Since the conventional, commercial processes for the preparation of MMP involve liquid-phase reactions, the need to condense the gaseous acrolein product has been considered unavoidable. However, further enhancements in the safety of handling acrolein and the process efficiency of manufacturing MMP could be achieved if the acrolein were transferred to the MMP reactor in the vapor phase, i.e., without significant condensation of the acrolein.

SUMMARY OF THE INVENTION

By the present invention, improved, continuous processes for the conversion of propylene to MMP are provided via the production of acrolein as an intermediate.

In one aspect of the present invention, the acrolein produced in the process is condensed and reacted with methyl mercaptan in a liquid phase to form MMP. In this aspect of the invention, the acrolein reaction is conducted in the presence of a recycle gas containing an effective amount of propane to enhance the efficiency of the acrolein reaction. Operation in this manner represents an improvement over the current processes in several ways. For example, the recycle process of the present invention can provide better distribution of the reaction load over the catalyst resulting in improved acrolein reaction efficiency and less by-product acrylic acid. In addition, in the present processes, oxygen rather than air, as is conventionally used, is fed to the acrolein reactor and unconverted propylene and oxygen are recycled to the acrolein reactor feed rather than purged and incinerated, which is necessary in an air-based process to avoid a build-up of nitrogen. The increased utilization of raw materials can substantially reduce operating expenses.

Also, equipment requirements for acrolein recovery can be reduced by the present process. More specifically, in the present process, it is not necessary to remove acetaldehyde from the acrolein product prior to the MMP reaction. Instead, the acetaldehyde can be preferably removed from the MMP reaction product. As a result, the acetaldehyde removal can be conducted in a small distillation column, e.g., 3 theoretical trays, versus a much larger column when the acetaldehyde is removed from the acrolein product, e.g., 40 theoretical trays.

In addition, in accordance with a preferred aspect of the present invention, the MMP reaction is continuous and is directly coupled to the acrolein process. Storage of significant volumes of highly purified acrolein, which is required in order to provide inventory for a batchwise MMP reaction, is eliminated and a much higher level of inherent process safety can be achieved.

In another aspect of the invention, propane is used as the feed source. Existing processes for MMP production typically use propylene as a feedstock for the production of acrolein, which is a process intermediate. Propane is substantially cheaper than propylene, as well as being more widely available and more stable in price. In a preferred aspect of the present invention, oxydehydrogenation is used for the conversion of propane to propylene. This is particularly well-suited for integration of the propane conversion step and the MMP process. By operating at low propane conversions, the selectivity to propylene can be made quite high, e.g., between 80 and 100 mole percent. Since the feed to the acrolein reactor need only contain propylene in low concentration, e.g., 5 to 40 mole percent, the low conversion/high selectivity mode of operation can be highly efficient provided unreacted propane is recycled to the oxydehydrogenation reactor. Such recycle operation is feasible because typical oxydehydrocatalysts are unaffected by species such as carbon oxides and water which are formed in the acrolein reactor. Hence, after recovery of the acrolein, the noncondensable gas stream may be recycled without expensive purification steps.

In another aspect of the invention, the acrolein produced in the process is reacted with methyl mercaptan in a vapor phase to form MMP. Significant enhancements in reaction efficiency can be achieved by passing the acrolein product to the MMP reactor in the vapor phase. Preferably, this operation is made possible using a diluent which is anhydrous. The low water content of the effluent from the anhydrous diluent (only the water of reaction is present) makes direct introduction into the MMP reactor feasible. By-products in the crude acrolein stream pass unreacted through the MMP reactor.

DETAILED DESCRIPTION OF THE INVENTION

Figure 1:
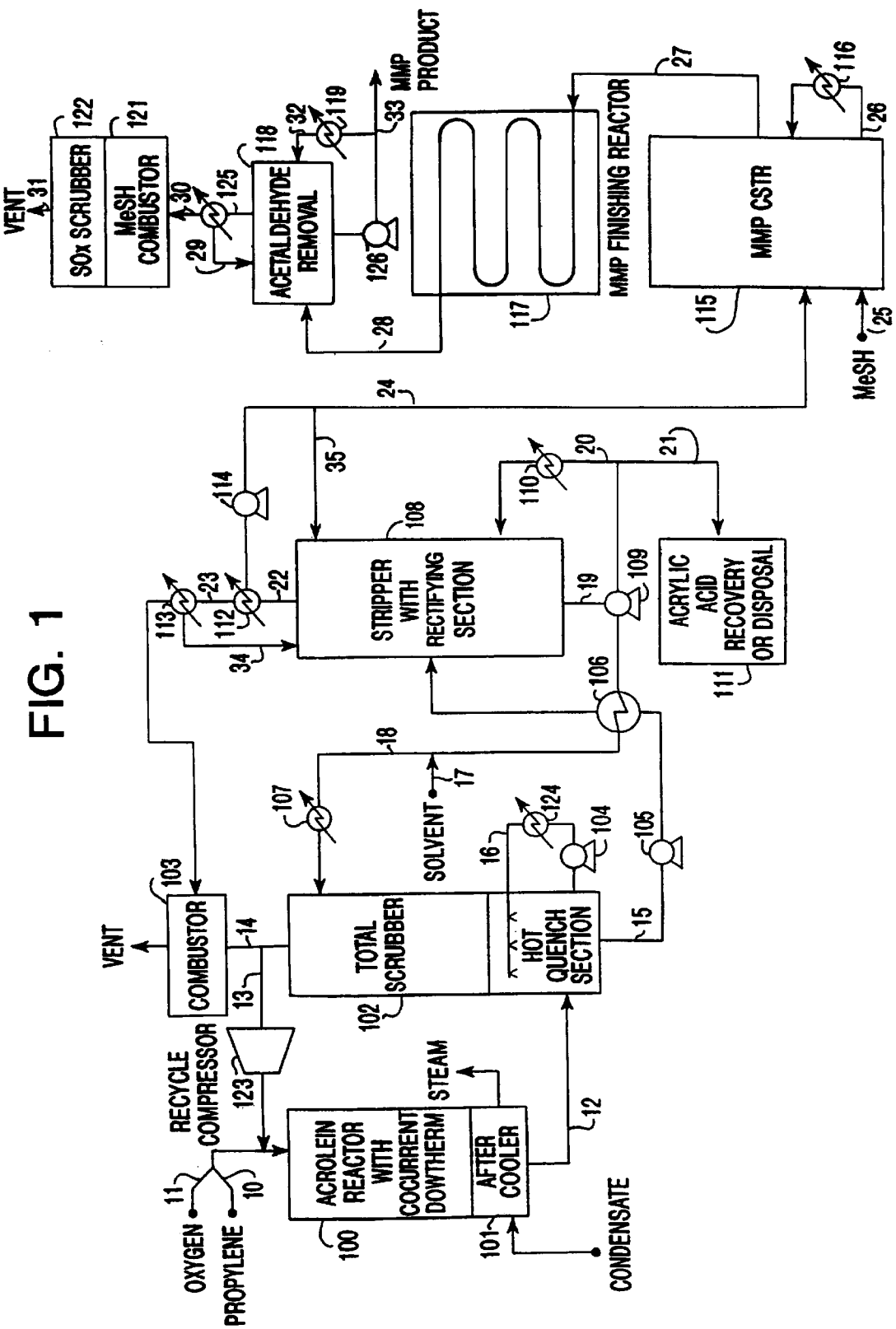
FIG. 1 is a simplified process flow diagram of a process for converting propylene to MMP in accordance with the present invention.

Propylene-containing feed streams suitable for use in the processes of the present invention can be obtained from common chemical sources known to those skilled in the art. For example, the propane-containing propylene which is obtained in the dehydrogenation of propane by thermal cracking or catalyzed dehydrogenation can be used as the feedstream. Such feed streams typically comprise at least 50 mole percent, preferably at least 90 mole percent, and more preferably at least 95 mole percent propylene. Such feed streams also typically contain propane and other light hydrocarbons.

When propane feed is used in the process of the present invention, the source of the propane is not critical. The purity of the starting material propane is not particularly limited, and a propane feed containing a lower alkane such as methane or ethane, air or carbon dioxide, as impurities, may be used. Typically, the feed will comprise at least 30 mole percent, preferably at least 50 mole percent and more preferably at least 80 mole percent propane.

The oxygen source for use in the processes of the present invention (both for propane oxidation and propylene oxidation) is not critical. However, the use of air is not preferred because the nitrogen content can adversely affect the ability to recycle effluent gases. Preferably, the oxygen source comprises at least 90 mole percent and more preferably at least 95 mole percent oxygen. The ratio of propane to oxygen varies with the desired conversion and the selectivity of the catalyst, but generally is in the range of 5/1–40/1. The reaction can also be conducted in the presence of diluents such as, for example, steam. Such diluents, when employed, can be fed at 0–50 times the partial pressure of the propane, with 0.2–10 times being usual.

In the propane-to-propylene reaction, it is preferred to employ a starting material gas which contains steam. In such a case, as a starting material gas to be supplied to the propane reactor, a gas mixture comprising steam-containing propane and an oxygen-containing gas, is usually used. However, the steam-containing propane and the oxygen-containing gas may be alternately supplied to the reaction system. The steam to be employed may be present in the form of steam gas in the reaction system, and the manner of its introduction is not particularly limited. However, steam is not essential in the process of the present invention.

Any catalyst effective for the conversion of propane to propylene is suitable for use in the present invention. Preferred catalysts include, for example, oxydehydrogenation catalysts which comprise promoted MoVNb oxides, vanadyl pyrophosphate and other oxydehydrogenation catalysts. Such catalysts and others suitable for the oxidation of propane are described, for example, in U.S. Pat. Nos. 4,148,757, 4,212,766, 4,260,822 and 5,198,580 and by E. M. Thorsteinson, T. P. Wilson, F. G. Young, and P. H. Kasai, J. Catal., 52, 116 (1978).

An example of a suitable catalyst for use in accordance with the present invention is a catalyst containing a mixed metal oxide comprising, as essential components, Mo, V, Te, O and X, wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron, indium and cerium, wherein the proportions of the respective essential components, based on the total amount of the essential components exclusive of oxygen, satisfy the following formulas:

$0.25 < r\ Mo < 0.98$ $0.003 < r\ V < 0.5$ $0.003 < r\ Te < 0.5$ $0.003 < rX < 0.5$ wherein r Mo, r V, r Te and r X are molar fractions of Mo, V, Te and X, respectively, based on the total amount of the essential components exclusive of oxygen. This catalyst is further described in U.S. Pat. No. 5,380,933.

For the propane oxidation, the reaction temperature is usually from about 200 to 550° C., preferably from about 250 to 450° C., more preferably from about 350 to 440° C. The gas hourly space velocity in the vapor-phase reaction is usually within a range of from about 100 to 10,000 hr$^{-1}$, preferably from about 300 to 6,000 hr$^{-1}$, more preferably from about 300 to 2,000 hr$^{-1}$. As used herein, "gas hourly space velocity" means the volume of reactant gas at standard conditions (0° C. and 1 atm pressure) passed over the catalyst in one hour divided by the total volume occupied by the catalyst. Further, as a diluting gas to adjust the space velocity and the oxygen partial pressure, an inert gas such as nitrogen, argon or helium may be employed. This reaction is typically conducted at a slightly elevated pressure, e.g., 2 to 6 atm.

Any suitable reactor sequence known to those skilled in the art may be used for the propane-to-propylene reaction. For example, the reaction can be conducted in a single stage, or can be conducted in two or more stages with oxygen introduction between the stages where introduction of the entire oxygen requirement at a single point could create flammable process mixtures. Further details on the conversion of propane to propylene and suitable equipment, e.g., reactors, are known to those skilled in the art.

In the propane-to-propylene reaction, particularly in the case of the propane oxydehydrogenation reaction, the propylene selectivity decreases with increasing propane conversion. Preferably, the propane-to-propylene reaction is conducted to provide for relatively low conversions of propane with high selectivities to propylene. More specifically, it is preferred that the conversion of propane be from about 5 to 40 percent and more preferably from about 10 to 30 percent. As used herein, the term "propane conversion" means the percentage of propane fed which is reacted. It is preferred that the selectivity of the conversion of propane to propylene be from about 50 to 98 percent and more preferably from about 80 to 98 percent. As used herein, the term "propylene selectivity" means the moles of propylene produced per mole of propane reacted expressed as a percentage.

In the present invention, propylene and oxygen are reacted over a catalyst at elevated temperature to produce acrolein. Water is a co-product of the reaction. A number of by-products are formed including carbon monoxide, carbon dioxide, formaldehyde, acetaldehyde, acetic acid and acrylic acid. Neither the propylene nor the oxygen in the reactor feed is totally converted. The noncondensable components in the reaction product, e.g., oxygen, propylene, carbon monoxide, carbon dioxide, propane and other light hydrocarbons, are separated from the condensable organic compounds, compressed and preferably recycled to the reactor inlet. In this way, utilization of oxygen and propylene can be very high.

In the aspect of the invention where the acrolein is passed to the MMP reactor in the vapor phase, the propylene-to-acrolein reaction is preferably conducted in the presence of an essentially anhydrous diluent gas such as described in U.S. Pat. No. 5,198,578. The essentially anhydrous diluent gas typically comprises a mixture of nitrogen, carbon dioxide, methane, ethane and propane; however, any other essentially anhydrous inert gas can be included. Some other useful inert gases include helium, argon, hydrogen, saturated hydrocarbon gases, $N_2O$, and carbon monoxide. When water is present as a trace impurity in any of the materials introduced into the reactors, at the elevated temperature required for these reactions the water is immediately converted to steam.

In other aspects of the present invention, some steam, e.g., about 0.3 to 8 moles per moles of propylene, may be utilized in the propylene-to-acrolein reaction. In these aspects, the steam may be effective in promoting the process possibly because it facilitates the desorption of the main products of the catalytic vapor-phase oxidation of propylene, i.e., acrolein and acrylic acid, or possibly because it participates directly in the reaction.

The propylene-to-acrolein reaction is not dependent upon any particular catalyst and any catalysts effective for the conversion of propylene to acrolein may be used. Typical catalysts are molybdenum-bismuth-iron-based mixed-metal-oxide oxidation catalysts, such as, for example, those disclosed in U.S. Pat. Nos. 3,825,600, 3,649,930, 4,339,355, 5,077,434 or 5,218,146. It may also be possible to conduct both the propane-to-propylene and propylene-to-acrolein reactions in a single reactor with one or more stages.

An example of a catalyst suitable for the propylene-to-acrolein reaction is an oxide catalyst containing Mo, Fe, and Bi. This catalyst is represented by the following general formula:

$$Mo_a W_b Bi_c Fe_d A_e B_f C_g D_h O_x$$

wherein Mo is molybdenum, Bi is bismuth, W is tungsten, Fe is iron, O is oxygen, A is at least one element selected from the group consisting of nickel and cobalt, B is at least one element selected from the group consisting of alkali metals, alkaline earth metals, and thallium, C is at least one element selected from the group consisting of phosphorus, arsenic, boron, and niobium, and D is at least one element selected from the group consisting of silicon, aluminum, and titanium, and the subscripts a, b, c, d, e, f, g, h, and x are respectively the numbers of atoms of the elements Mo, W, Bi, Fe, A, B, C, D, and O, providing that a=2 to 10, b=0 to 10, on condition that a+b=12, c=0.1 to 10.0 d=0.1 to 10, e=2 to 20, f=0.005 to 3.0, g=0 to 4, h=0.5 to 15, and x is a number required to satisfy the valance requirements of the other elements. This catalyst is described in U.S. Pat. No. 5,218, 146.

The catalysts for use in the processes of the present invention may be in the form of pellets, beads, or rings containing a through hole which are produced by a tabletting machine or an extruding machine or otherwise in a form having catalytic components deposited on a refractory carrier. Suitable propylene-to-acrolein catalysts are commercially available, for example, from Nippon Shokubai, Tokyo, Japan; Nippon Kayaku, Tokyo, Japan; and Mitsubishi, Tokyo, Japan.

As regards the acrolein reaction gas composition, the content of propylene is in the range of 5 to 30 volume percent, preferably 7 to 15 volume percent, that of oxygen in the range of 8 to 40 volume percent, preferably 12 to 30 volume percent, that of a saturated aliphatic hydrocarbon having 1 to 5 carbon atoms, preferably 1 to 3 carbon atoms, e.g., propane, in the range of 5 to 70 volume percent, preferably 10 to 60 volume percent, that of carbon monoxide in the range of 0 to 50 volume percent, preferably 15 to 45 volume percent, that of carbon dioxide in the range of 0 to 50 volume percent, preferably 5 to 40 volume percent, (providing that the total content of the hydrocarbon, carbon monoxide and carbon dioxide is in the range of 40 to 90 volume percent, preferably 60 to 85 volume percent), and that of steam, when present, in the range of 0 to 50 volume percent, preferably 5 to 40 volume percent, (providing that the molar ratio of steam to propylene is in the range of 0.3 to 8, preferably 0.3 to 5), the molar ratio of oxygen to propylene is in the range of 1.0 to 2.5, preferably 1.5 to 2.0, and the contact time is in the range of 0.3 to 1.5 seconds, preferably 0.5 to 1.2 seconds. The catalyst is preferably capable of effecting a conversion of propylene of not less than 70 mole percent, preferably not less than 80 mole percent.

Preferably, the concentration of propane in the feedstream to the acrolein reaction zone is from about 5 to 70 volume percent, more preferably from about 10 to 60 volume percent and most preferably from about 10 to 40 volume percent, based on the total volume of the feedstream. As used herein, the terms "mole percent" and "volume percent" are equivalent as they relate to the concentrations of components in vapor streams.

Quite surprisingly, it has been found that the propylene-to-acrolein reaction efficiency can be substantially enhanced when using propane-containing feedstreams as described above. Preferably, the acrolein reaction efficiency is from about 65 to 97 percent and more preferably from about 75 to 90 percent. As used herein, the term "propylene-to-acrolein reaction efficiency" means moles acrolein produced per mole propylene fed expressed as a percentage.

Typically, approximate ranges for feed compositions are defined based on the generalized operating constraints discussed above. Propylene-to-acrolein reaction feeds in the following quantities are typically particularly useful:

Propylene: Up to about 16 g-mole per hour/liter of acrolein reaction catalyst, preferably up to about 10 g-mole per hour/liter of acrolein reaction catalyst;

Oxygen: 1.1 to 2.1:1 $O_2/C_3H_6$ ratio, such that there is up to about 33.6 g-mole per hour O2/liter of acrolein reaction catalyst, preferably up to about 21 g-mole per hour $O_2$ liter of acrolein reaction catalyst;

Diluent: About 0.7 to 16:1 inert diluent/$C_3H_6$ ratio, preferably 2 to 10:1 inert diluent/$C_3H_6$ ratio.

The general reaction conditions are not narrowly critical, and are those known to the art. The propylene-to-acrolein reaction operates at temperatures of about 250 to 450° C., although temperatures of about 270 to 425° C. are preferred.

Operating pressures of about 1 to 4 atm are typical, although subatmospheric, atmospheric, or superatmospheric pressures may be used. Preferred commercial modes of operation will often minimize pressures, but pressures are typically held in the 2- to 3-atm range due to system pressure-drop constraints.

Flow rates can be varied to achieve contact times of from about 0.2 to 2 seconds in the propylene-to-acrolein reaction; however, typical commercial flows provide about 0.3 to 1.5 seconds contact time. Contact times of about 0.5 to 1.2 seconds are preferred. As used herein, "contact time" is defined as the ratio of the open volume in the catalyst bed to the process volumetric flow at process conditions.

The type of reactor used in the conversion of propylene to acrolein is not critical and may be, for example, a fixed-bed, tubular-flow reactor with liquid coolant passed through the shell. Fluidized bed reactors may also be employed. Further details of suitable reactors are known to those skilled in the art.

In accordance with the present invention, it is not necessary to highly purify the acrolein product prior to passing it to the MMP reactor. Also, it is not necessary to remove acetaldehyde from the acrolein product. Instead, the acetaldehyde can be removed from the MMP reaction product. As a result, the acetaldehyde removal can be conducted in a small distillation column, e.g., 3 theoretical trays, versus a much larger column when the acetaldehyde is removed from the acrolein product, e.g., 40 theoretical trays. Accordingly, as described in more detail below, the acrolein product may only need to be subjected to mild scrubbing and fractionation prior to being passed to the MMP reactor. If water is used as a scrubbing solvent, sufficient water must be removed in the fractionation step to avoid forming a two-phase liquid acrolein product.

Typically, the acrolein product stream to be fed to the MMP reaction zone will comprise from about 0.5 to 3.5 weight percent, and preferably from about 1.0 to 2.5 weight percent acetaldehyde, from about 88 to 97 weight percent, preferably from about 93 to 97 weight percent acrolein, and from about 2 to 8 weight percent, preferably from about 2 to 4 weight percent water, based on the total weight of the acrolein product stream.

The acrolein-to-MMP reaction may be carried out, for example, at a temperature between about 30 and 80° C., preferably between about 40 and 70° C., for liquid-phase operation, and at a temperature of from about 80 to 400° C., preferably from about 150 to 300° C. and more preferably from about 180 to 260° C. for vapor-phase operation. The pressure is not critical and is typically between about 2 and 4 atmospheres. Methyl mercaptan and acrolein are preferably introduced into the reactor in a mercaptan-to-acrolein molar ratio of between about 0.95 and 1.2, but most preferably between about 1.00 and 1.02. Methyl mercaptan can be readily commercially obtained.

By establishing a very slight excess of mercaptan in the reactant mixture, conversion of acrolein is maximized and the need for disposition of unreacted acrolein is essentially obviated. Where the molar ratio of reactants is controlled in the range of between about 1.00 and 1.02 moles methyl mercaptan per mole of acrolein, direct reaction between the mercaptan and acrolein is effected in preference to formation of by-products. As a consequence, a high rate of reaction is realized, with high productivity and relatively low capital and operating expense of the reactor. The reactant ratio may be controlled by various means known in the art.

Conventional catalysts and catalyst concentrations may be used for the reaction. Such catalysts include a wide variety of organic amines such as, for example, pyridine, hexamethyltetraamine, or triethylamine. Organic acids are typically included to inhibit polymerization of acrolein. Where, for example, a pyridinium acetate catalyst is used, the concentration is maintained at between about 0.2 and 1.0 weight percent, preferably between about 0.35 and 0.5 weight percent by continuous or periodic additions of catalyst to the reaction medium.

The vapor-phase reaction can also be run without a catalyst. Preferably, the MMP reaction is conducted with at least 10 weight percent of the MMP in the vapor phase, preferably with at least 20 weight percent of the MMP in the vapor phase, more preferably with at least 50 weight percent of the MMP in the vapor phase, and most preferably with at least 80 weight percent of the MMP in the vapor phase, based on the total weight of MMP in the MMP reactor.

Any reactor suitable for the conversion of acrolein to MMP may be employed in the process of the present invention. Such reactors include, for example, liquid/gas contacting reactors such as described in U.S. Pat. No. 5,352,837, tubular plug-flow reactors, continuous stirred tank reactors, and other back-mixed reactors. Various combinations of two or more reactors may also be used to good advantage. Either a plug-flow reactor with high recycle or a continuous stirred tank reactor followed by a plug-flow reactor is preferred. Further details of suitable reactors are known to those skilled in the art.

The MMP product obtained from the process of the present invention, after purification and recovery known to those skilled in the art, may be used, for example, for the production of methionine and other compounds such as described in U.S. Pat. No. 5,386,056.

The invention is hereafter described with reference to the Figures which is not intended to limit the scope of the claims that follow.

With reference to FIG. 1, a feed containing about 90 volume percent propylene and 10 volume percent propane in stream 10 is combined with oxygen in stream 11 and with compressed recycle gas in stream 13 at a pressure of about 30 to 60 psia. The combined gas stream comprising 7 to 30 volume percent propylene, 9 to 30 volume percent oxygen, 10 to 30 volume percent propane, 10 to 40 volume percent carbon dioxide, 15 to 45 volume percent carbon monoxide and 0 to 5 volume percent water vapor is fed to acrolein reactor 100 where about 75 to 99 mole percent of the propylene is converted to acrolein, various by-products and water over a mixed molybdenum-bismuth-iron-oxide catalyst at 300 to 425° C. Reactor 100 is a liquid-cooled, multitube reactor wherein the catalyst is in the tubes. The by-products consist mainly of formaldehyde, carbon monoxide, carbon dioxide, acetaldehyde, allyl alcohol, acetic acid and acrylic acid. The hot reaction gases exiting the reactor are cooled to 200 to 280° C. by exchanging heat against condensate (water) in aftercooler 101 to produce steam.

The cooled reactor product gases in stream 12 are fed to a hot quench section of total scrubber 102. In the hot quench section, the hot gases are contacted directly with circulating liquid solvent stream 16 to cool and condense a portion of the gases. The solvent may be water which is used in the process of FIG. 1, or it may be another compound having absorptivity for acrolein and acrylic acid, e.g., diethylene glycol, propylene glycol, other glycols, diols and glycol ethers, and tributyl phosphate, and other solvents known to those skilled in the art. The circulating liquid solvent stream is withdrawn from the base of the total scrubber by pump 104 and pumped through heat exchanger 124 where it gives up some of its heat to cooling water. A portion of the reaction gases leaves the hot quench section of the total scrubber and enters the upper portion of the total scrubber. In the upper portion of the scrubber the gases are contacted directly by a downflowing stream of liquid solvent in stream 18. The solvent in stream 18 is the same compound as comprises stream 16. Before entering the scrubber stream 18 passes through heat exchanger 107 where it gives up some of its heat to cooling water. The temperature in scrubber 102 can range from about 30 to 70° C. when water is the solvent and from about 70 to 250° C. when other solvents are used. The pressure in scrubber 102 can range from about 15 to 40 psia, for example. Scrubber 102 contains about 15 theoretical stages and can contain trays or packing known to those skilled in the art.

An overhead stream comprising unreacted oxygen and propylene, propane, carbon monoxide, carbon dioxide and water vapor with small amounts of organic compounds exits the total scrubber and is split into two parts, stream 13 and stream 14. Stream 13 is compressed in recycle compressor 123 wherein it is pressurized to 15 to 60 psia and combined with fresh propylene and oxygen as feed to the reactor. Stream 14 is a purge stream which rids the process of propane, carbon monoxide and carbon dioxide so these components do not build up to excessive levels. Stream 14 is 1 to 5 percent of the total volume of gases leaving the top of the total scrubber. Stream 14 is incinerated in combustor 103 and the incineration products vented to the atmosphere.

The liquid product from the total scrubber, stream 15, comprises about 75 to 95 weight percent water, about 2 to 20 weight percent acrylic acid and about 1 to 3 weight percent acrolein and is withdrawn from the bottom of the scrubber and pumped by pump 105 through heat exchanger 106 where heat is transferred from stream 18. Stream 15 is fed to stripper column 108 which contains about 15 theoretical stages above the feed point and about 7 stages below the feed point. Stripper column 108 operates at a temperature of from about 50 to 200° C. at the bottom and about 30 to 100° C. at the top. In stripper 108 the total scrubber liquid product is separated into a liquid-product stream 19 and a vapor-product stream 22. Stream 19 comprises about 75 to 98 weight percent solvent, e.g., water, and 2 to 20 weight percent acrylic acid and is withdrawn from the base of the stripper column by pump 109. The discharge of pump 109 is split into three parts, stream 18, stream 20 and stream 21. Stream 18 passes through heat exchanger 106 where it gives up some of its heat to stream 15 and flows to total scrubber 102 where it serves as the scrubbing solvent. Stream 17 is makeup solvent to the process. Stream 20 passes through reboiler 110 where it is heated and returned to stripper column 108. Stream 21 flows to the acrylic acid recovery or disposal system 111. Further details of acrylic acid handling are known to those skilled in the art and are described, for example, in U.S. Pat. No. 4,999,452.

Stream 22 exits the stripper column overhead as a vapor comprising of 88 to 97 weight percent acrolein, 2 to 8 weight percent water and 1 to 4 weight percent other organic compounds. In condenser 112, most of stream 22 is condensed against cooling water and is pumped from the condenser as a liquid by pump 114 and split into a majority stream 24 and a minority stream 35. Stream 35 is returned to the top of the stripper column as reflux. Stream 24 is the liquid acrolein product for the MMP reaction. A small vapor stream 23 exits the stripper condenser and flows to vent condenser 113. In the vent condenser some additional vapor is condensed against refrigerated coolant with the condensate stream 34 returned to the stripper column as reflux. The noncondensable gases leaving the vent condenser are routed to combustor 103 for incineration.

Stream 24 is fed to continuous stirred tank reactor ("CSTR") 115. Methyl mercaptan is also fed to CSTR 115 as stream 25. The molar ratio of acrolein to methyl mercaptan is preferably closely controlled at a value close to unity to maximize MMP efficiency. A soluble catalyst is used, typically an amine. Pyridinium acetate is a preferred catalyst. CSTR 115 provides a liquid residence time of about two hours at 60 to 65° C. and a pressure of about 30 to 60 psia.

The reaction of acrolein and methyl mercaptan is exothermic. Heat is removed from CSTR 115 by withdrawing a portion of the contents as stream 26 and passing it through heat exchanger 116 where it gives up some of its heat to cooling water. The liquid product from CSTR 115, comprising 92 to 97 weight percent MMP, 3 to 8 weight percent water, unreacted acrolein and methyl mercaptan, and other organics, flows as stream 27 to MMP finishing reactor 117. Finishing reactor 117 is a tubular reactor containing pyridinium acetate catalyst providing about one hour of residence time during which more acrolein and methyl mercaptan react to provide greater than 99.5 mole percent acrolein conversion. Heat is not removed from finishing reactor 117 so the liquid temperature increases about 5° C. The pressure in reactor 117 is about 30 to 60 psia.

Stream 28 leaving the finishing reactor comprises 95 to 97 weight percent MMP, 1 to 4 weight percent water, about one weight percent acetaldehyde and small amounts of other organic compounds. In acetaldehyde removal column 118 stream 28 is split into two parts, a liquid tails product and a vapor overhead product. Removal column 118 contains about 3 theoretical stages and operates at a pressure of about 0 to 15 psia and a temperature of about 30 to 70° C. The liquid tails product is pumped from the bottom of the column by pump 126 and is split into stream 32 and stream 33. Stream 32 flows through reboiler 119 and returns to acetaldehyde removal column 118. Stream 33 comprises 96 to 99 weight percent MMP, about 1 to 3 weight percent water, and about 1000 ppmw acetaldehyde is the MMP product from the process. The overhead vapor product from the acetaldehyde removal column enters condenser 125 where a portion of the vapor is condensed and returned to the column as reflux. The uncondensed portion of the vapor product exits the condenser to methyl mercaptan ("MeSH") combustor 121 for incineration. The incineration products are scrubbed to remove sulfur oxides in SOx scrubber 122 before being vented to the atmosphere. Further details of scrubbing technology are known to those skilled in the art. See, for example, U.S. Pat No. 5,019,361.

In this aspect of the invention, there is provided a process for producing methylmercaptopropanal comprising:

(i) passing a propylene feedstream comprising propylene, oxygen and a recycle gas comprising propane, oxygen and at least one of carbon monoxide or carbon dioxide to an acrolein reaction zone wherein the feedstream is contacted with an acrolein reaction catalyst at conditions effective to promote the formation of acrolein;

(ii) withdrawing an acrolein effluent stream comprising acrolein, propane, acetaldehyde and water from the acrolein reaction zone;

(iii) passing the acrolein effluent stream to an acrolein absorption zone wherein the acrolein effluent stream is contacted with a solvent having absorptivity for acrolein;

(iv) withdrawing a first vapor stream comprising the recycle gas and a first liquid stream comprising acrolein, acetaldehyde, water and the solvent from the acrolein absorption zone;

(v) recycling at least a portion of the first vapor stream to the acrolein reaction zone wherein the recycle gas stream comprises an effective amount of propane to enhance the efficiency of acrolein formation in the acrolein reaction zone;

(vi) passing the first liquid stream to a fractionation zone to separate the first liquid stream into a second vapor stream comprising acrolein, acetaldehyde and water and a second liquid stream containing acrylic acid, water and the solvent;

(vii) condensing the second vapor stream to form an acrolein product stream and passing the condensed liquid and liquid MeSH to a MMP reaction zone and contacting the acrolein and methyl mercaptan with a MMP reaction catalyst at conditions effective to promote the conversion of acrolein and methyl mercaptan to MMP;

(viii) withdrawing a MMP effluent stream comprising MMP and acetaldehyde from the MMP reaction zone; and (ix) separating the MMP effluent stream into a liquid product stream comprising MMP and a vapor product stream comprising acetaldehyde.

Figure 2:
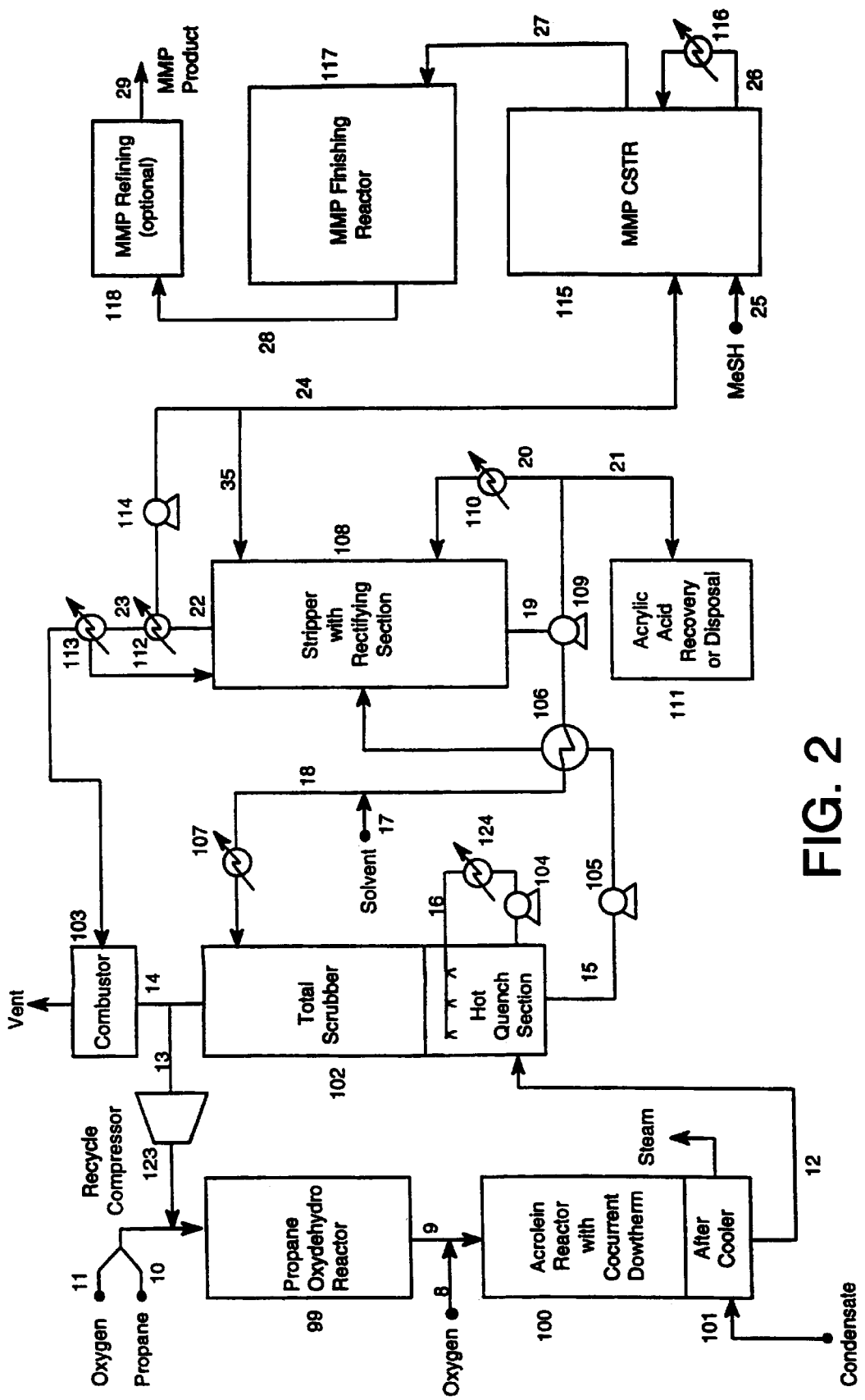
FIG. 2 is a simplified process flow diagram of a process for converting propane to MMP in accordance with the present invention.

With reference to FIG. 2, a feed containing about 90 volume percent propane in stream 10 is combined with oxygen in stream 11 and with compressed recycle gas in stream 13 at a pressure of about 30 to 90 psia and are fed to a reactor 99 containing a heterogeneous oxidative dehydrogenation catalyst (such as one of the preferred catalysts described above). The oxygen feed may be pure, or an air feed may be used. Recycle stream 13 is also fed to reactor 99. Stream 13 contains unconverted propane and oxygen which passed through the process without conversion at an earlier time. Stream 13 also contains propylene and water and various noncondensable gases which are not reactive in the process. Nonreactive gases would include, but not be limited to, carbon dioxide and carbon monoxide, and for the air-based process, nitrogen. All feed streams are preheated to approximately the operating temperature of reactor 99, which operates at no greater than 500° C. The pressure of the feed streams is slightly greater than the reactor pressure, which is between 30 and 90 psia. The gaseous species and the solid catalyst are contacted effectively in the reactor, which may have various designs including fixed or fluidized catalyst beds. The propane conversion to propylene is in the range of 5 to 40 percent. The gas product stream 9 contains the propylene product, unreacted propane and oxygen, water, small amounts of by-products, and the nonreactive feed species.

The crude propylene product stream 9 is passed directly, without purification, to the propylene oxidation reactor 100 where the contained propylene is oxidized to acrolein and/or acrylic acid. Additional oxygen is fed to reactor 100 in stream 8. Reactor 100 contains a heterogeneous catalyst for the oxidation of propylene (such as one of the preferred catalysts described above). The gaseous reactant and solid catalyst are contacted effectively in the reactor, which may have various designs including fixed or fluidized catalyst beds. Reactor 100 operates in the temperature range of 300 to 425° C. and a pressure range of 25 to 85 psia. The conversion of the contained propylene is approximately 90 percent, but may be in the range of 70 to 100 percent. The principal product is acrolein with acrylic acid being a minor co-product. The effluent stream 12 is immediately cooled to approximately 250 ° C. in aftercooler 101. Stream 12 has a pressure of approximately 20 psia, but it can range from 15 to 50 psia.

A wide variety of recovery and refining schemes may be employed to separate acrolein from effluent stream 12. One attractive scheme is presented in FIG. 2 for illustration, although numerous other effective schemes may be possible. Upon entering scrubber 102, stream 12 is cooled further via direct contacting with a liquid quench stream before passing into the scrubber section. The scrubbing liquid may be water, as used in current practice, or it may be any suitable solvent having a substantial capacity for absorbing acrolein. The condensable species, which are primarily acrolein, acrylic acid and water, are condensed by and mix with the scrubbing solvent. The remaining noncondensable species vent from the top of scrubber 102. Most of the vented material is recycled to the feed of reactor 100 in stream 13, after passing through compressor 123. A small purge stream 14 is routed to combustor 103 and subsequently vented from the process. Upon leaving the scrubber, the liquid solvent stream 15 has a temperature and pressure of approximately 50 ° C. and 20 psia, although these values may vary over a considerable range in order to optimize the process for a particular solvent. The temperature of stream 15 increases after it is pumped through heat exchanger and picks up heat from stream 18. The magnitude of the temperature increase depends largely upon the physical properties of the specific solvent used.

Stream 15 is fed to stripper/rectifier 108 above a section of stripping trays and below a section of rectification trays. Vapor created in heat exchanger 110 in the column bottom strips the acrolein product from the solvent in the stripping section. By contrast, the heavier acrylic acid concentrates in the liquid-solvent phase. The bottoms stream 19 is divided into three streams, i.e., 18, 20 and 21. The temperature of stream 19 will depend upon the solvent used, but will be low enough to avoid significant fouling from acrylic acid reaction. Stream 18 is cooled by indirect contact with stream 15 in exchanger 106 and, if necessary, by indirect contact with a cooling medium in exchanger 107, before being fed to the top of scrubber 102. Stream 20 is heated and partially or totally vaporized in heat exchanger 110, and the resulting vapor is returned to column 108. Stream 21, containing essentially all the acrylic acid produced in reactor 100, is sent to a separate unit for recovery or disposal of the acrylic acid.

The acrolein stripped in the lower section of column 108 enters the rectification section in which it is contacted with countercurrent reflux from streams 35 and 113. The product stream 22 is condensed primarily in heat exchanger 112. Uncondensed species pass to a second, lower-temperature condenser 113 in stream 23; thus all species but noncondensable gases are removed, and the remaining gases are routed to combustor 103. The condensed acrolein product is passed to the MMP reactor via stream 24 without additional purification. The purity of stream 24 depends upon the solvent characteristics and the specific design and operation of the rectifying section. The acrolein composition in stream 24 typically would be between 88 and 97 weight percent acrolein. If desired, a vapor-phase acrolein stream could be fed to the MMP reactor simply by conducting a partial, rather than total condensation, in heat exchanger 112.

Stream 24 and the methyl mercaptan feed stream 25 are fed to MMP reactor 115, the design of which may vary widely. Either feed stream may be a vapor or a liquid, as desired. The heat of the exothermic reaction is removed in heat exchanger 116. The product stream 27 from reactor 115 is predominantly MMP product with some residual unconverted reactants. Stream 27 may or may not require a finishing reactor step. If needed, stream 27 is routed to a finishing reactor 117 for additional conversion of reactants. The product stream 28 may optionally be sent to additional refining operation(s) such as fractionation known to those skilled in the art 118 as indicated. Stream 29 contains the completed MMP product.

Figure 3:
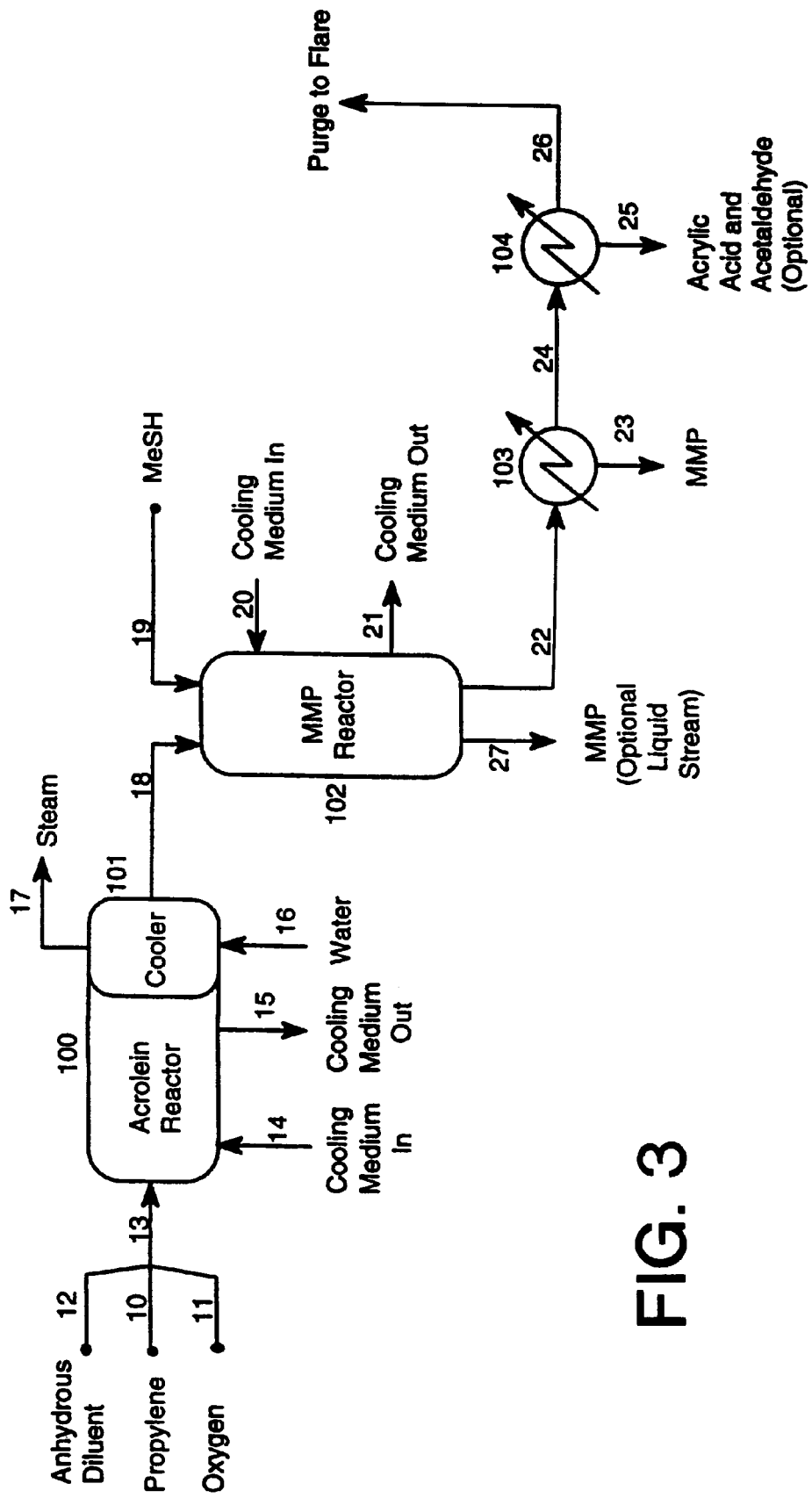
FIG. 3 is a simplified process flow diagram of a process for converting propylene to MMP in the vapor phase in accordance with the present invention.

With reference to FIG. 3, a propylene stream 10 comprising 90 mole percent propylene and 10 mole percent propane, an oxygen stream 11 and an anhydrous diluent stream 12 comprising methane, ethane and propane are mixed to form stream 13 and fed to acrolein reactor 100. All feeds are gas-phase. Various other different diluent species known to those skilled in the art are possible within the scope of the present invention. The mixed feed stream 13 consists of 7 to 15 mole percent propylene, 10 to 30 percent oxygen and the remainder diluent. The feed streams have pressures slightly greater than the operating pressure of reactor 100, which is in the range of 30 to 60 psia. The feed streams are preheated to approximately the operating temperature of the reactor 100, which is in the range of 300 to 450° C. Reactor 100 is a liquid-cooled, multitube reactor wherein the catalyst is in the tubes. Heat from the exothermic reaction must be removed to control the temperature of reactor 100. The optimal heat removal technique depends upon the specific design of reactor 100. One possible approach is illustrated in which the heat is removed using a circulating heat transfer medium. The catalyst in reactor 100 is a mixed molybdenum-bismuth-iron-oxide catalyst.

Seventy five to 100 percent of the propylene is converted to acrolein and various by-products, which include acrylic acid, water, carbon monoxide, carbon dioxide, allyl alcohol, acetaldehyde, formaldehyde and others in reactor 100. The product gases are immediately cooled to between 200 and 300° C. in cooler 101, which is close-coupled to reactor 100. The sensible heat of the product gas can be removed by indirectly contacting the hot gas with water in a heat exchanger to generate steam as shown in streams 16 and 17. Other heat removal techniques are possible. The cooled product stream 18 exits the cooler and is fed directly to the vapor-phase MMP reactor 102. Additional heat removal from stream 18 may be dictated before entering reactor 102, depending upon the reactor operating temperature. The reaction can be carried out in the temperature range from 80 to 400° C, depending upon the specific reactor design. Vapor-phase methyl mercaptan is fed to the reactor 102 in stream 19. The ratio of methyl mercaptan to acrolein will generally be close to unity, although deviations from this are possible for certain reactor operating schemes.

Reactor 102 may contain a heterogeneous catalyst or it may contain an inert solid packing to aid mixing. In the latter case, a homogenous catalyst may or may not be fed to the reactor. The vapor-phase reaction of acrolein and methyl mercaptan may be conducted either way. If using a heterogeneous catalyst, the design of reactor 102 is such that the gaseous reactants and solid catalyst are effectively contacted. For this purpose, reactor 102 may have various designs including either a fixed or fluidized catalyst bed. If no catalyst is used, reactor 102 is designed in such a way as to mix the two feed streams effectively. Backmixing or plug flow or an intermediate contacting pattern are possible. The heat of reaction must be removed from reactor 102. The heat removal technique will depend upon the specific design of the reactor. One possible approach is illustrated and utilizes circulation of a heat transfer medium through reactor 102 via streams 20 and 21.

Reactor 102 may be operated such that the MMP product either remains in the vapor phase until after discharge in stream 22 or is partially condensed within the reactor. Any condensed MMP is removed from the reactor via stream 27. Vapor-phase MMP in stream 22 is condensed in heat exchanger 103, with a liquid MMP product stream 23 being produced. The remaining vapors and permanent gases pass from exchanger 103 in stream 24. If desired, vapor-phase acrylic acid and acetaldehyde may be recovered by condensation in heat exchanger 104, which is operated at a lower temperature than exchanger 103. The permanent gases and any remaining vapors are discharged from exchanger 104 and routed to a flare or incinerator.

EXAMPLES

The following examples are provided for illustrative purposes and are not intended to limit the scope of the claims which follow.

EXAMPLE 1

In Example 1, acrolein and methyl mercaptan liquid feeds were vaporized and co-fed in a downward direction to a heated reactor tube which was 38 cm (14.9 in) long and 1.02 cm (0.40 in) in inside diameter. The reactor tube was filled with a solid packing which is identified in the example.

The product exiting the bottom of the reactor passed through a simple jacketed-tube condenser/cooler at 10° C. and was collected in a product vessel. Liquid-product samples for analysis were obtained with a syringe from the outlet of the condenser/cooler.

EXAMPLE 1-A
Vapor-Phase MMP Reaction Over Stainless Steel Packing

The reactor tube was filled with $\frac{1}{16}$-in size protruded stainless steel Pro-Pak® packing available from Chem-Pro Corporation, Fairfield, N.J.

Results of the runs are shown in the following table. Both runs were made at approximately 204 KPa (15 psig) reactor pressure. Concentrations of MMP and heavies, i.e., components exiting the gas chromatograph after MMP, are reported on a MeSH-and-acrolein-free basis.

TABLE 1

| Run | Rxtr Temp ° C. Top/ Bottom | MeSH Feed g/min | Acrolein Feed g/min | MeSH/ Acrolein Molar Ratio | MMP wt % | Heavies wt % |
|---|---|---|---|---|---|---|
| 1 | 190/205 | 1.31 | 1.55 | 1.00 | 87.5 | 12.5 |
| 2 | 235/255 | 1.31 | 1.55 | 1.00 | 80.9 | 19.1 |

At both temperatures the predominant reaction product is MMP.

EXAMPLE 1-B
Vapor-Phase MMP Reaction Over Stainless Steel Packing and Solid CaO Fragments The first 28 cm of the reactor tube were filled with $\frac{1}{16}$-in size protruded stainless steel Pro-Pak® packing. The remaining 10 cm of tube length were filled with 14–30 mesh fragments of a calcium oxide catalyst.

Results of the runs are shown in the following table. Both runs were made at approximately 204 KPa (15 psig) reactor pressure. Concentrations of MMP and heavies, components exiting the gas chromatograph after MMP, are reported on a MeSH-and-acrolein-free basis.

TABLE 2

| Run | Rxtr Temp ° C. Top/ Bottom | MeSH Feed g/min | Acrolein Feed g/min | MeSH/ Acrolein Molar Ratio | MMP wt % | Heavies wt % |
|---|---|---|---|---|---|---|
| 1 | 186/206 | 1.30 | 1.54 | 1.00 | 84.4 | 15.6 |
| 2 | 225/254 | 1.31 | 1.54 | 1.01 | 86.8 | 13.2 |

As in the preceding example, the predominant reaction product is MMP at both run temperatures.

EXAMPLE 2

This example shows the effect of utilizing propane to improve the efficiency of the reaction of propylene to acrolein. The experiments were carried out in a pilot-scale reactor system of two single reactor tubes of typical commercial dimensions. The first reactor tube contained a commercial propylene-to-acrolein catalyst which is comprised of bismuth, molybdenum, and iron oxides and other promoters, i.e., ACF-2, available from Nippon Shokubai. The second stage, which was close-coupled to the first, contained a commercial acrolein-to-acrylic acid catalyst comprised of bismuth, molybdenum, and iron oxides and other promoters, i.e., ACS-4, available from Nippon Shokubai. The second stage was used as an effective means of converting acrolein for disposal. Each stage had a jacket of a heat transfer fluid to remove heat of reaction. Thermocouples were placed strategically to measure hot spots in each system. The gaseous reactants were introduced via gas mass flow meters. The pressure at the entrance of the first stage was held at a constant 28 psig. The final product out of the second stage was passed through a scrubber and then condensed to equilibrium at 4° C., leaving only noncondensables. Concentration measurements of the feed, first-stage effluent, second-stage effluent, and the recycle stream were obtained via a gas chromatograph. Fresh propylene feed concentration was held at 8.2 mole percent and the gas hourly space velocity held at 1800 $hr^{-1}$.

EXAMPLE 2-A

A baseline experiment was run with a 303° C. jacket temperature, 12.1 mole percent feed oxygen concentration, 49.3 mole percent feed nitrogen concentration, 30.0 mole percent steam concentration, and 0.3 mole percent feed propane concentration. Overall, the process was once-through only with no recycle. In the first stage, 90.5 percent of the feed propylene was consumed by the reaction. Of the propylene consumed, 79.9 percent went directly to forming acrolein in the first-stage outlet. Overall, 72.3 percent of the propylene fed to the system ends up as the useful product acrolein, while the rest is essentially lost. To make 3.8 standard liters per minute ("slm") of acrolein, 5.3 slm of propylene are required. This experiment is representative of typical commercial operation.

EXAMPLE 2-B

In comparison, a recycle process was run with a high concentration of propane at similar conditions of active ingredients. The experiment was run with a jacket temperature of 303° C., 14.1 mole percent feed oxygen concentration, 8.7 mole percent feed water concentration, and 6.2 mole percent propane concentration. Essentially no nitrogen was in the feed. 98–99 percent of the second-stage noncondensable gases were returned to feed of the first stage to maintain constant pressure levels. In the first stage, 90.6 percent of the feed propylene was consumed by reaction. Of the propylene consumed, 87.6 percent went directly to forming acrolein in the first-stage outlet. Overall, 87.5 percent of the propylene fed to the system ends up as acrolein. To make 3.8 slm of acrolein, 4.4 slm of propylene is required. The experiment requires only 83 percent of the propylene required for once-through operation.

The improvement in propylene utilization arises from two factors. The first is the nearly complete recycling of unreacted material back to the front of the reactor. This accounts for 60 percent of the decrease in propylene requirements. The second factor is the presence of the relatively high concentration of propane in the feed. This increased concentration increases the flowing heat capacity and reduced temperatures in the system considerably. Overall, this effect accounts for 40 percent of the observed improvement in propylene usage.

Propane is introduced to the process as an impurity in the propylene feed. The propane levels of this experiment are consistent with 1–2 mole percent impurity level. Recycle operation makes economically viable the use of lower-purity propylene which can be more cost effective.

Although the invention has been described with respect to specific aspects, those skilled in the art will recognize that other aspects are intended to be within the scope of the claims that follow.

We claim:

1. A process for producing methylmercaptopropanal ("MMP") comprising:

(i) passing a propane feedstream comprising propane, oxygen and a recycle gas comprising propane, oxygen and at least one of carbon monoxide or carbon dioxide to a propylene reaction zone at conditions to promote the formation of propylene to provide a preliminary oxidation effluent stream comprising propylene, propane, oxygen and at least one of carbon monoxide or carbon dioxide;

(ii) passing the preliminary oxidation effluent stream to an acrolein reaction zone wherein the preliminary oxidation effluent stream is contacted with an acrolein reaction catalyst at conditions effective to promote the formation of acrolein to provide an acrolein effluent stream comprising acrolein, propane, acetaldehyde and water;

(iii) passing the acrolein effluent stream to an acrolein separation zone wherein the acrolein effluent stream is partially condensed to provide a liquid acrolein product stream, comprising acrolein, acetaldehyde and water and a recycle gas stream comprising the recycle gas;

(iv) passing the acrolein product stream and methyl mercaptan to a MMP reaction zone and contacting the acrolein and methyl mercaptan with a MMP reaction catalyst at conditions effective to promote the conversion of acrolein and methyl mercaptan to MMP; and (v) recycling at least a portion of the recycle gas stream to the acrolein reaction zone;

wherein the preliminary oxidation effluent stream comprises an effective amount of propane to enhance the efficiency of acrolein formation in the acrolein reaction zone.

2. The process of claim 1 wherein the concentration of propane in the preliminary oxidation effluent stream is from about 5 to 70 volume percent.

3. The process of claim 1 wherein the acrolein product stream comprises from about 0.5 to 3.5 weight percent acetaldehyde.

4. The process of claim 1 wherein the acrolein product stream comprises from about 88 to 97 weight percent acrolein.

5. The process of claim 1 which further comprises withdrawing a MMP effluent stream comprising MMP and acetaldehyde from the MMP reaction zone; and separating the MMP effluent stream into a liquid-product stream comprising MMP and a vapor-product stream comprising acetaldehyde.

6. The process of claim 1 wherein the contacting of the acrolein and methyl mercaptan is conducted with both the acrolein and the methyl mercaptan in a liquid phase.

7. The process of claim 1 wherein steps (i) to v are conducted in a continuous fashion.

* * * * *